(12) United States Patent
Zergiebel et al.

(10) Patent No.: US 11,547,394 B2
(45) Date of Patent: *Jan. 10, 2023

(54) ADAPTER ASSEMBLIES FOR INTERCONNECTING SURGICAL LOADING UNITS AND HANDLE ASSEMBLIES

(71) Applicant: Covidien LP, Mansfield, MA (US)

(72) Inventors: Earl M. Zergiebel, Guilford, CT (US); David Chowaniec, Rocky Hill, CT (US); Ryan Williams, New Hartford, CT (US); Anand Subramanian, Stamford, CT (US)

(73) Assignee: COVIDIEN LP, Mansfield, MA (US)

( * ) Notice: Subject to any disclaimer, the term of this patent is extended or adjusted under 35 U.S.C. 154(b) by 1052 days.

This patent is subject to a terminal disclaimer.

(21) Appl. No.: 16/227,362

(22) Filed: Dec. 20, 2018

(65) Prior Publication Data
US 2019/0122840 A1  Apr. 25, 2019

Related U.S. Application Data

(63) Continuation of application No. 14/672,579, filed on Mar. 30, 2015, now Pat. No. 10,163,589.
(Continued)

(51) Int. Cl.
*A61B 17/00* (2006.01)
*H01H 21/22* (2006.01)
(Continued)

(52) U.S. Cl.
CPC .. *A61B 17/00234* (2013.01); *A61B 17/07207* (2013.01); *A61B 90/90* (2016.02);
(Continued)

(58) Field of Classification Search
CPC ............ A61B 90/90; A61B 2017/0046; A61B 2017/00477; A61B 2090/0808
See application file for complete search history.

(56) References Cited

U.S. PATENT DOCUMENTS 2,777,340 A   1/1957   Hettwer et al.
2,957,353 A   10/1960  Babacz
(Continued)

FOREIGN PATENT DOCUMENTS

AU   2008229795 A1   4/2009
CA      2451558 A1   1/2003
(Continued)

OTHER PUBLICATIONS

Extended European Search Report corresponding to International Application No. EP 15 15 1076.5 dated Apr. 22, 2015.
(Continued)

*Primary Examiner* — Christopher A Flory
(74) *Attorney, Agent, or Firm* — Carter, DeLuca & Farrell, LLP

(57) ABSTRACT

An adapter assembly configured to be coupled to a surgical loading unit includes a switch, an elongated member, and an annular member. The switch is configured to be toggled in response to the surgical loading unit being coupled to the adapter assembly. The elongated member is in communication with the switch and is resiliently biased in a distal direction toward a locking position in which the switch is toggled. The annular member is disposed adjacent the elongated member and is rotatable between a first orientation, in which the annular member prevents distal movement of the elongated member, and a second orientation, in which the elongated member moves distally to toggle the switch.

18 Claims, 8 Drawing Sheets

Related U.S. Application Data

(60) Provisional application No. 62/017,581, filed on Jun. 26, 2014.

(51) Int. Cl.
*H01H 9/20* (2006.01)
*A61B 17/072* (2006.01)
*A61B 90/90* (2016.01)
*A61B 90/00* (2016.01)
*H01H 9/28* (2006.01)

(52) U.S. Cl.
CPC .............. *H01H 9/20* (2013.01); *H01H 21/22* (2013.01); *A61B 2017/0046* (2013.01); *A61B 2017/00353* (2013.01); *A61B 2017/00398* (2013.01); *A61B 2017/00464* (2013.01); *A61B 2017/00473* (2013.01); *A61B 2017/00477* (2013.01); *A61B 2090/0807* (2016.02); *A61B 2090/0808* (2016.02); *H01H 9/287* (2013.01); *H01H 2221/016* (2013.01); *H01H 2231/048* (2013.01); *H01H 2235/00* (2013.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |

(56) References Cited

U.S. PATENT DOCUMENTS

| | | |
|---|---|---|
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 3,016,178 A1 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,163,589 B2 | 12/2018 | Zergiebel et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |

(56) References Cited

U.S. PATENT DOCUMENTS

| | | |
|---|---|---|
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0179375 A1* | 7/2008 | Scirica ............. A61B 17/07207 227/176.1 |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1* | 12/2011 | Swensgard ............. A61B 34/70 606/130 |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0092719 A1* | 4/2013 | Kostrzewski ........ A61B 17/068 227/177.1 |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |

(56) References Cited

FOREIGN PATENT DOCUMENTS

| | | |
|---|---|---|
| EP | 2676615 A2 | 12/2013 |
| ES | 2333509 A1 | 2/2010 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

ADAPTER ASSEMBLIES FOR INTERCONNECTING SURGICAL LOADING UNITS AND HANDLE ASSEMBLIES

CROSS-REFERENCE TO RELATED APPLICATION

This application is a continuation application of U.S. patent application Ser. No. 14/672,579, filed on Mar. 30, 2015, which claims the benefit of and priority to U.S. Provisional Patent Application Ser. No. 62/017,581, filed on Jun. 26, 2014, the entire contents of each of which being incorporated by reference herein.

BACKGROUND

1. Technical Field

The present disclosure relates to adapter assemblies for use with an electromechanical surgical system and their methods of use. More specifically, the present disclosure relates to hand-held, electromechanical surgical instruments capable of detecting a presence of a loading unit and/or identifying one or more parameters of a loading unit attached to an adapter assembly.

2. Background of Related Art

Linear clamping, cutting, and stapling surgical devices may be employed in surgical procedures to resect tissue. Conventional linear clamping, cutting, and stapling devices include a handle assembly, an elongated shaft and a distal portion. The distal portion includes a pair of scissors-styled gripping members, which clamp about the tissue. In this device, one or both of the two scissors-styled gripping members, such as the anvil portion, moves or pivots relative to the overall structure. The actuation of this scissoring device may be controlled by a grip trigger maintained in the handle.

In addition to the scissoring device, the distal portion may also include a stapling mechanism. One of the gripping members of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a reusable handle assembly and a disposable loading unit or the like that is selectively coupled to the handle assembly prior to use and then disconnected from the handle assembly following use in order to be disposed of or in some instances sterilized for re-use.

A need exists for various types of adapter assemblies that communicate relevant information to a handle assembly upon a proper engagement of a loading unit with a handle assembly.

SUMMARY

The present disclosure relates to adapter assemblies for use between handle assemblies and loading units. The present disclosure also relates to mechanisms for toggling a switch of an adapter assembly for effectively communicating information about a loading unit to a handle assembly, which is coupled to the adapter assembly, upon engagement of the loading unit with the handle assembly.

According to an aspect of the present disclosure, an adapter assembly is provided. The adapter assembly is configured to be coupled to a surgical loading unit. The adapter assembly includes a switch, an elongated member, and an annular member. The switch is configured to be toggled in response to the surgical loading unit being coupled to the adapter assembly. The elongated member is in communication with the switch and is resiliently biased in a distal direction toward a locking position in which the switch is toggled. The annular member is disposed adjacent the elongated member and is rotatable between a first orientation, in which the annular member prevents distal movement of the elongated member, and a second orientation, in which the elongated member moves distally to toggle the switch.

In embodiments, the annular member may be resiliently biased toward the first orientation such that the annular member rotates to the first orientation upon a decoupling of the loading unit from the adapter assembly. The adapter assembly may further include a biasing member engaged to the annular member. The biasing member may be configured to resist rotation of the annular member from the first orientation to the second orientation. It is contemplated that the biasing member may be a leaf spring having a fixed proximal end and a distal end in engagement with the annular member. A rotation of the annular member may pivot the leaf spring about the proximal end thereof.

In embodiments, the annular member may include at least one appendage configured to abut the loading unit upon coupling the loading unit with the adapter assembly. The at least one appendage may include a first tab circumferentially disposed on the annular member and a second tab circumferentially disposed on the annular member and radially spaced from the first tab. The first tab may be engaged with a distal end of the elongated member when the annular member is in the first orientation.

In embodiments, a proximal end of the elongated member may include a ring member configured to toggle the switch when the elongated member is in the locking position. The ring member may be proximal of the switch and not engaged therewith when the elongated member is in a non-locking position.

In embodiments, the adapter assembly may further include an inner housing and an actuator board. The inner housing has a proximal end and the elongated member has a proximal end disposed around the proximal end of the inner housing. The switch may be disposed within the proximal end of the inner housing. The actuator board may be attached to the proximal end of the inner housing and extend proximally therefrom and overlap the switch. The actuator board may be resiliently biased toward a position in which the actuator board is spaced from the switch. The proximal end of the elongated member biases the actuator board into engagement with the switch upon movement of the elongated member to the locking position.

In another aspect of the present disclosure, a surgical instrument is provided. The surgical instrument includes a surgical loading unit and an adapter assembly. The loading unit has a proximal end including at least one protrusion. The adapter assembly has a proximal end configured to be coupled to a handle assembly and a distal end configured to be coupled to the proximal end of the loading unit. The adapter assembly includes a switch, an elongated member, and an annular member. The switch is configured to be toggled in response to the loading unit being coupled to the distal end of the adapter assembly. The elongated member has a proximal end in communication with the switch and a distal end. The elongated member is resiliently biased in a distal direction away from a non-locking position and toward a locking position in which the switch is toggled. The annular member is disposed adjacent the distal end of the elongated member and includes at least one appendage configured to abut the at least one protrusion of the loading unit upon coupling the loading unit with the adapter assembly. The annular member is rotatable between a first orientation, in which the at least one appendage is engaged to the distal end of the elongated member to maintain the elongated member in the non-locking position and a second orientation, in which the at least one appendage is disengaged from the distal end of the elongated member such that the elongated member moves to the locking position to toggle the switch.

In embodiments, the annular member may be resiliently biased toward the first orientation such that the annular member rotates to the first orientation upon a decoupling of the loading unit from the adapter assembly. The adapter assembly may further include a biasing member engaged to the annular member and may be configured to resist rotation of the annular member from the first orientation to the second orientation. The biasing member may be a leaf spring having a proximal end fixed to the adapter assembly and a distal end in engagement with the annular member. A rotation of the annular member pivots the leaf spring about the proximal end thereof.

In embodiments, in the locking position, the at least one protrusion is captured between the at least one appendage and the distal end of the elongated member such that the loading unit is lockingly engaged to the adapter assembly.

In embodiments, the at least one appendage may include a first tab circumferentially disposed on the annular member and a second tab circumferentially disposed on the annular member and radially spaced from the first tab. The first tab engages with the distal end of the elongated member when the annular member is in the first orientation. The at least one protrusion may include a first protrusion and a second protrusion radially spaced from the first protrusion. Upon coupling of the loading unit with the adapter assembly the first tab engages the first protrusion and the second tab engages the second protrusion.

In embodiments, the proximal end of the elongated member includes a ring member configured to toggle the switch when the elongated member is in the locking position. The ring member may be engaged with the switch when the elongated member is in the locking position and the ring member may be proximal of the switch and not engaged therewith when the elongated member is in the non-locking position.

In yet another aspect of the present disclosure, another embodiment of a surgical instrument is provided. The surgical instrument includes a handle assembly, a surgical loading unit, and an adapter assembly. The surgical loading unit has a proximal end including at least one protrusion. The adapter assembly has a proximal end configured to be coupled to the handle assembly and a distal end configured to be coupled to the proximal end of the loading unit. The adapter assembly includes a switch, an elongated member, and an annular member. The switch is configured to be toggled in response to the loading unit being coupled to the distal end of the adapter assembly. The switch is electrically connected with the handle assembly such that upon engagement of the loading unit with the adapter assembly the switch communicates to the handle assembly at least one of an indicator that the loading unit is coupled to the adapter assembly or at least one parameter pertaining to the loading unit. The elongated member has a proximal end in communication with the switch and a distal end. The elongated member is resiliently biased in a distal direction away from a non-locking position and toward a locking position in which the switch is toggled. The annular member is disposed adjacent the distal end of the elongated member and includes at least one appendage configured to abut the at least one protrusion of the loading unit upon coupling the loading unit with the adapter assembly. The annular member is rotatable between a first orientation, in which the at least one appendage is engaged to the distal end of the elongated member to maintain the elongated member in the non-locking position and a second orientation, in which the at least one appendage is disengaged from the distal end of the elongated member such that the elongated member moves to the locking position to toggle the switch.

BRIEF DESCRIPTION OF THE DRAWINGS

Embodiments of the present disclosure are described herein with reference to the accompanying drawings, wherein.

DETAILED DESCRIPTION

Figure 1A:
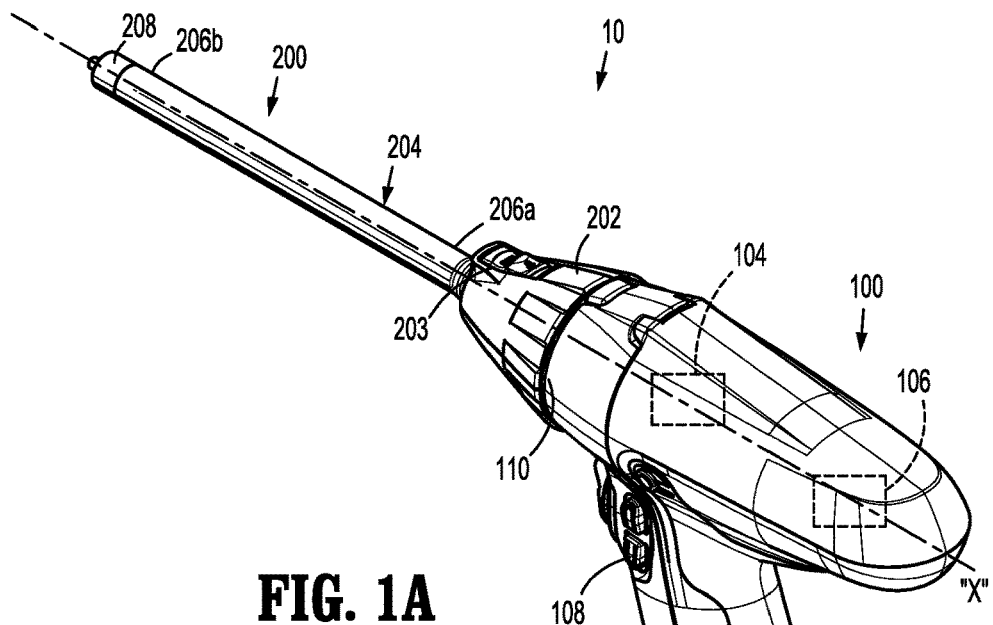
FIG. 1A is a perspective view of a hand-held, electromechanical surgical instrument, in accordance with an embodiment of the present disclosure.

Embodiments of the presently disclosed surgical instruments, surgical loading units, and adapter assemblies for electromechanical surgical devices and/or handle assemblies are described in detail with reference to the drawings, in which like reference numerals designate identical or corresponding elements in each of the several views. As used herein the term "distal" refers to that portion of the surgical instrument, adapter assembly, handle assembly, loading unit or components thereof, farther from the user, while the term "proximal" refers to that portion of the surgical instrument, adapter assembly, handle assembly, loading unit or components thereof, closer to the user. As used herein, the term "toggle" is defined as a transition between a first condition, in which a switch is engaged, and a second condition, in which the switch is disengaged.

Figure 1B:
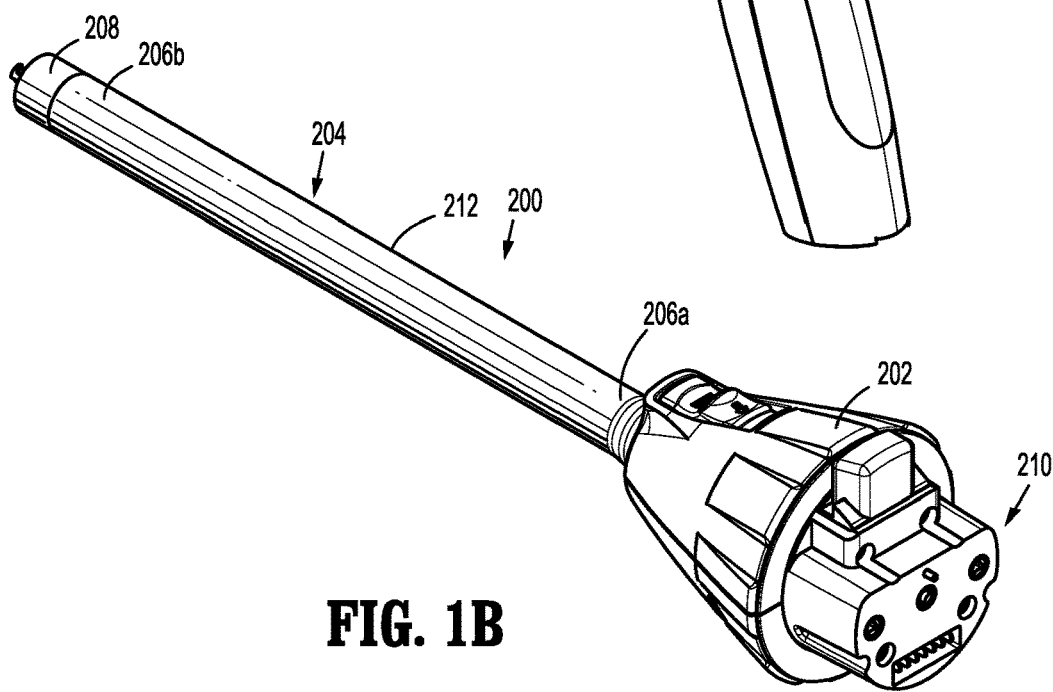
FIG. 1B is a perspective view of an embodiment of an adapter assembly of the surgical instrument shown in FIG. 1A.
Figure 1C:
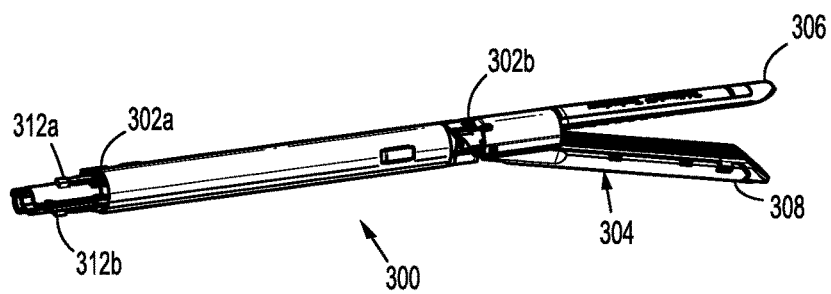
FIG. 1C is a side view of a surgical loading unit of the surgical instrument shown in FIG. 1A, including an end effector attached thereto.

With reference to FIGS. 1A-1C, a surgical instrument, in accordance with an embodiment of the present disclosure, is generally designated as 10, and is in the form of a powered, hand-held, electromechanical surgical instrument configured for selective attachment thereto with any one of a number of adapter assemblies 200, and, in turn, each unique adapter assembly 200 is configured for selective connection with any number of surgical loading units 300. Loading unit 300 and adapter assembly 200 are configured for actuation and manipulation by a handle assembly 100.

Reference may be made to International Publication No. WO 2009/039506 and U.S. Patent Application Publication No. 2011/0121049, the entire contents of all of which are incorporated herein by reference, for a detailed description of the construction and operation of an exemplary electromechanical, hand-held, powered surgical instrument.

Handle assembly 100 includes one or more controllers (not shown), a power source (not shown), a processor 104, and a drive mechanism having one or more motors 106, gear selector boxes (not shown), gearing mechanisms (not shown), and the like. Processor 104 is configured to control motors 106 and to detect a presence of a loading unit, for example, loading unit 300, and/or determine one or more parameters of loading unit 300, as described herein. Handle assembly 100 further includes a control assembly 108. Control assembly 108 may include one or more finger-actuated control buttons, rocker devices, joystick or other directional controls, whose input is transferred to the drive mechanism to actuate adapter assembly 200 and loading unit 300.

In particular, with reference to FIG. 1C, the drive mechanism is configured to drive shafts and/or gear components in order to selectively move an end effector 304 of loading unit 300 to rotate end effector 304 about a longitudinal axis "X" defined by surgical instrument 10 relative to handle assembly 100, to move an anvil assembly 306 relative to a cartridge assembly 308 of end effector 304, and/or to fire a stapling and cutting cartridge within cartridge assembly 308 of end effector 304.

With continued reference to FIG. 1A, handle assembly 100 defines a nose or connecting portion 110 configured to accept a corresponding drive coupling assembly 210 (FIG. 1B) of adapter assembly 200. Connecting portion 110 of handle assembly 100 has a cylindrical recess (not shown) that receives drive coupling assembly 210 of adapter assembly 200 when adapter assembly 200 is mated to handle assembly 100. Connecting portion 110 houses one or more rotatable drive connectors (not shown) that interface with corresponding rotatable connector sleeves of adapter assembly 200.

When adapter assembly 200 is mated to handle assembly 100, each of the rotatable drive connectors of handle assembly 100 couples with a corresponding rotatable connector sleeve of adapter assembly 200. In this regard, the interface between the plurality of drive connectors of handle assembly 100 and the plurality of corresponding connector sleeves of the adapter assembly are keyed such that rotation of each of the drive connectors causes rotation of the corresponding connector sleeves of adapter assembly 200.

The mating of the drive connectors of handle assembly 100 with the connector sleeves of adapter assembly 200 allows rotational forces to be independently transmitted via each of the three respective connector interfaces. The drive connectors of handle assembly 100 are configured to be independently rotated by the drive mechanism.

Since each of the drive connectors of handle assembly 100 has a keyed and/or substantially non-rotatable interface with the respective connector sleeves of adapter assembly 200, when adapter assembly 200 is coupled to handle assembly 100, rotational force(s) are selectively transferred from drive mechanism of handle assembly 100 to adapter assembly 200.

With continued reference to FIGS. 1A-1C, the selective rotation of drive connector(s) of handle assembly 100 allows surgical instrument 10 to selectively actuate different functions of end effector 304. Selective and independent rotation of first drive connector of handle assembly 100 corresponds to the selective and independent opening and closing of end effector 304, and driving of a stapling/cutting component of end effector 304. Also, the selective and independent rotation of second drive connector of handle assembly 100 corresponds to the selective and independent articulation of end effector 304 about an articulation axis that is transverse to longitudinal axis "X." In particular, end effector 304 defines a second or respective longitudinal axis and is movable from a first position in which the second or respective longitudinal axis is substantially aligned with longitudinal axis "X" to at least a second position in which the second longitudinal axis is disposed at a non-zero angle with respect to longitudinal axis "X." Additionally, the selective and independent rotation of the third drive connector of handle assembly 100 corresponds to the selective and independent rotation of loading unit 300 about longitudinal axis "X" relative to handle assembly 100 of surgical instrument 10.

With continued reference to FIGS. 1A and 1B, adapter assembly 200 includes a knob housing 202 and an elongated body 204 extending from a distal end of knob housing 202. Knob housing 202 and elongated body 204 are configured and dimensioned to house the components of adapter assembly 200. Elongated body 204 is dimensioned for endoscopic insertion. For example, elongated body 204 is passable through a typical trocar port, cannula or the like. Knob housing 202 is dimensioned to not enter the trocar port, cannula of the like. Knob housing 202 includes a button 203 coupled to a switch 220 of adapter assembly 200, as described in greater detail below.

Figure 2A:
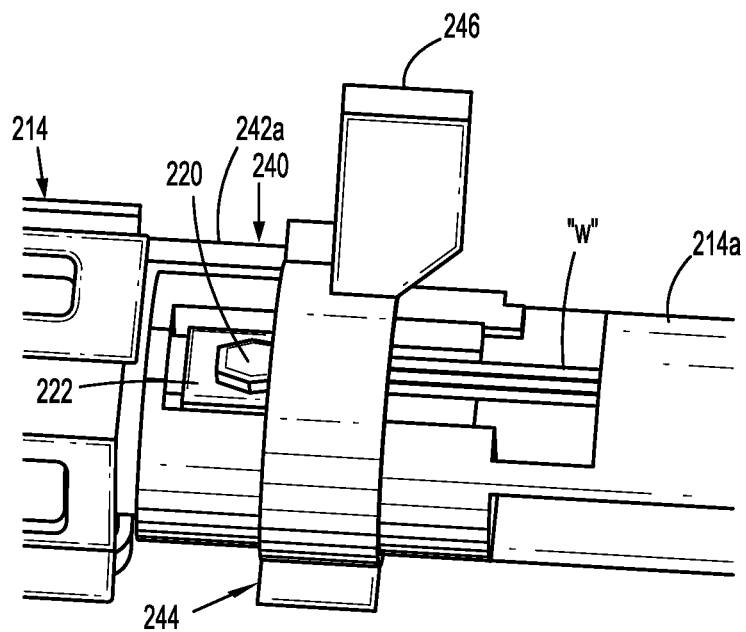
FIG. 2A is an enlarged operational view of a proximal portion of the adapter assembly shown in FIG. 1B and a switch thereof in a non-actuated state.
Figure 2B:
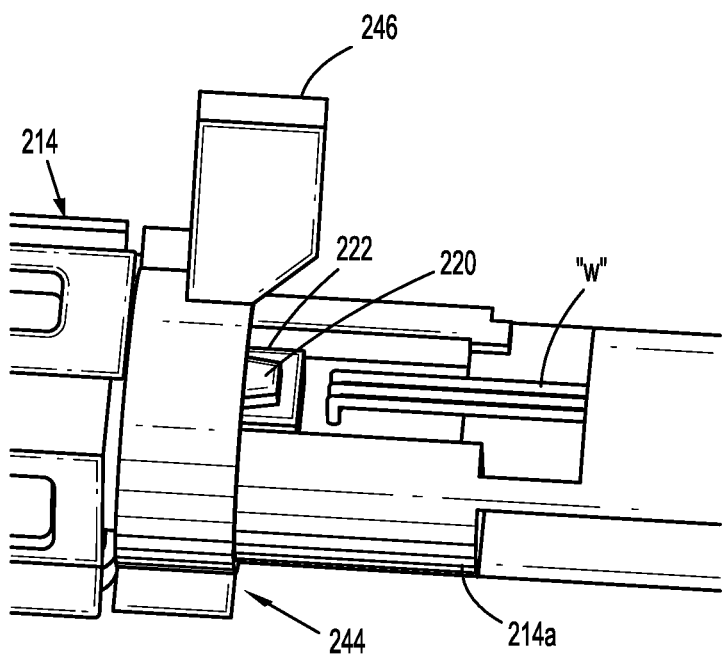
FIG. 2B is an enlarged operational view of the proximal portion of the adapter assembly shown in FIG. 1B and the switch thereof in an actuated state.

Elongated body 204 of adapter assembly 200 has a proximal portion 206a coupled to knob housing 202 and a distal portion 206b configured to be coupled to loading unit 300. Elongated body 204 includes a cylindrical outer housing 212 and a cylindrical inner housing 214 (FIGS. 2A, 2B)

disposed within outer housing 212. Elongated body 204 further includes a distal cap 208 extending distally from distal portion 206b.

With reference to FIG. 1C, coupling and decoupling of loading unit 300 is described. Loading unit 300 has a proximal portion 302a configured for engagement with distal end 206b of elongated body 204 of adapter assembly 200 and a distal portion 302b. Proximal portion 302a is sized and dimensioned to be inserted through distal cap 208 to lockingly engage adapter assembly 200 with loading unit 300. Proximal portion 302a includes a first protrusion or first lug 312a and a second protrusion or second lug 312b radially spaced from one another. Lugs 312a, 312b are each disposed on an outer surface of proximal portion 302a. Lugs 312a, 312b have a substantially rectangular cross-section. In embodiments, lugs 312a, 312b may be variously configured, such as, for example, those alternatives described herein. Upon coupling loading unit 300 with adapter assembly 200, lugs 312a, 312b engage or interface with tabs 268a, 268b of annular member, respectively, as described in greater detail below.

Distal portion 302b of loading unit 300 has an end effector 304 extending therefrom. End effector 304 is pivotally attached to distal portion 302b. End effector 304 includes an anvil assembly 306 and a cartridge assembly 308. Cartridge assembly 308 is pivotable in relation to anvil assembly 306 and is movable between an open or unclamped position and a closed or clamped position for insertion through a cannula of a trocar.

Reference may be made to U.S. Pat. No. 7,819,896, filed on Aug. 31, 2009, entitled "TOOL ASSEMBLY FOR A SURGICAL STAPLING DEVICE", the entire content of which is incorporated herein by reference, for a detailed discussion of the construction and operation of an end effector.

With reference to FIGS. 2A-6B, adapter assembly 200 further includes a switch 220, an elongated member or locking bar 240, an annular member 260, and a biasing member 280, each being disposed within elongated body 204 of adapter assembly 200. With specific reference to FIGS. 2A and 2B, switch 220 is toggled by a switch actuator or ring member 244 in response to a coupling of loading unit 300 to distal portion 206b of elongated body 204 as described in detail below. Switch 220 is disposed on or within inner housing 214, adjacent knob housing 202. Switch 220 is mounted on a printed circuit board 222 that is electrically connected to processor 104 of handle assembly 100 via electrical wires "W" and/or any other suitable connections, e.g., wireless communication. Upon toggling of switch 220, switch 220 communicates to handle assembly 100 that loading unit 300 is lockingly engaged to distal portion 206b of elongated body 204 or that loading unit 300 is disengaged from distal portion 206b of elongated body 204, as described in further detail below.

Figure 5A:
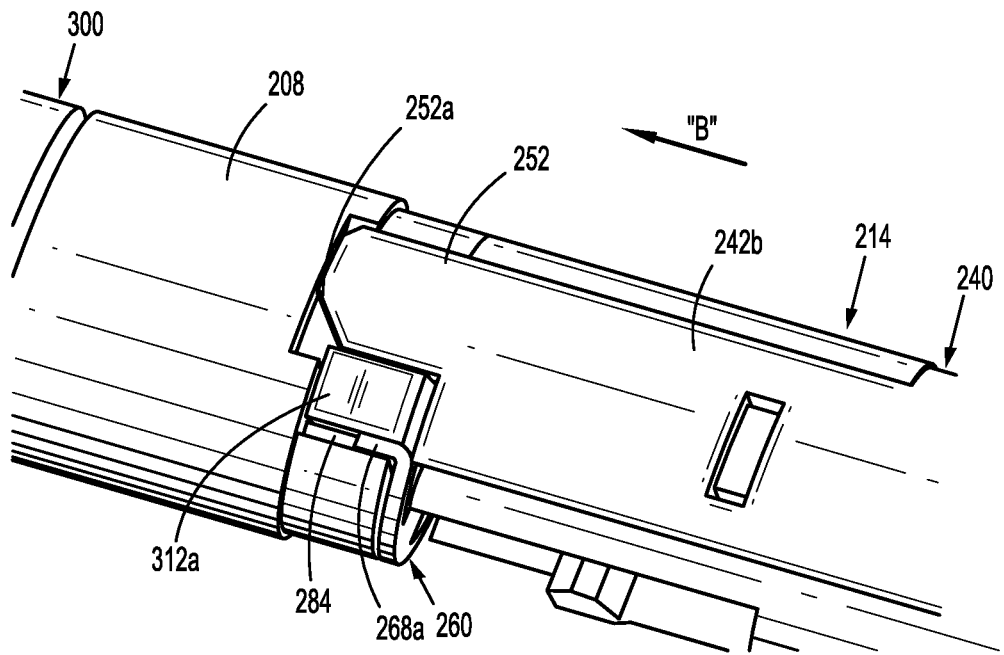
FIG. 5A is an enlarged operational view of the distal portion of the adapter assembly shown in FIG. 1B lockingly engaged with the loading unit shown in FIG. 1C.

With continued reference to FIGS. 2A and 2B, as mentioned above, adapter assembly 200 includes locking bar 240. Locking bar 240 is slidingly disposed within or along inner housing 214 of elongated body 204. Locking bar 240 is longitudinally movable between a proximal position or non-locking position, as shown in FIGS. 2A, 3A, 3B, and 5B, and a distal position or locking position, as shown in FIGS. 2B and 5A. Locking bar 240 toggles switch 220 during movement between the proximal/non-locking position and the distal/locking position. In embodiments, locking bar 240 may toggle switch 220 when in the distal/locking position or the proximal/non-locking position.

Locking bar 240 has a proximal end portion 242a disposed within knob housing 202 and a distal end portion 242b (see FIGS. 3A, 3B, 5A, and 5B) disposed within distal portion 206b of elongated body 204. Proximal end portion 242a includes ring member 244 configured to toggle switch 220 when locking bar 240 is in the distal/locking position. Ring member 244 encircles a proximal end 214a of inner housing 214 and is slidingly disposed therewith. Ring member 244 includes a fin 246 coupled to button 203 of knob housing 202, such that an actuation of button 203 results in a concomitant movement of locking bar 240.

In use, as locking bar 240 translates along longitudinal axis "X" (see FIG. 1A) from the proximal/non-locking position, as shown in FIGS. 2A, 3A, 3B, and 5B, to the distal/locking position, as shown in FIGS. 2B and 5A, ring member 244 of locking bar 240 toggles switch 220 by engaging switch 220. In embodiments, ring member 244 may include a projection (not shown) configured to engage switch 220 when locking bar 240 is in the distal/locking position. In some embodiments, ring member 244 actuates or depresses switch 220 when locking bar 240 is in the proximal/non-locking position and disengages switch 220 upon movement from the proximal/non-locking position to the distal/locking position depending on the location and orientation of switch 220.

Figure 3A:
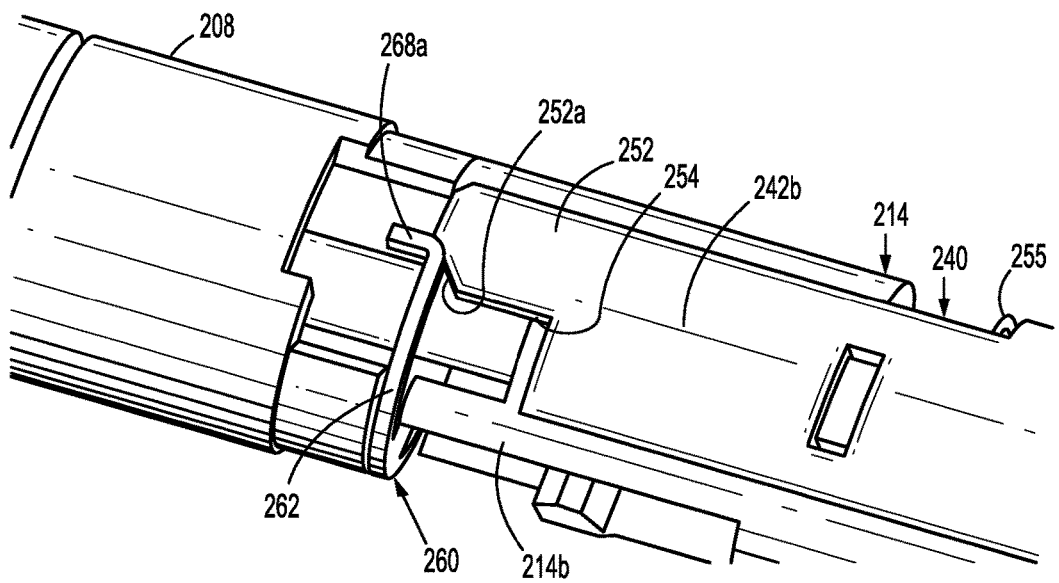
FIG. 3A is an enlarged operational view of a distal portion of the adapter assembly shown in FIG. 1B, without a loading unit engaged therewith.
Figure 3B:
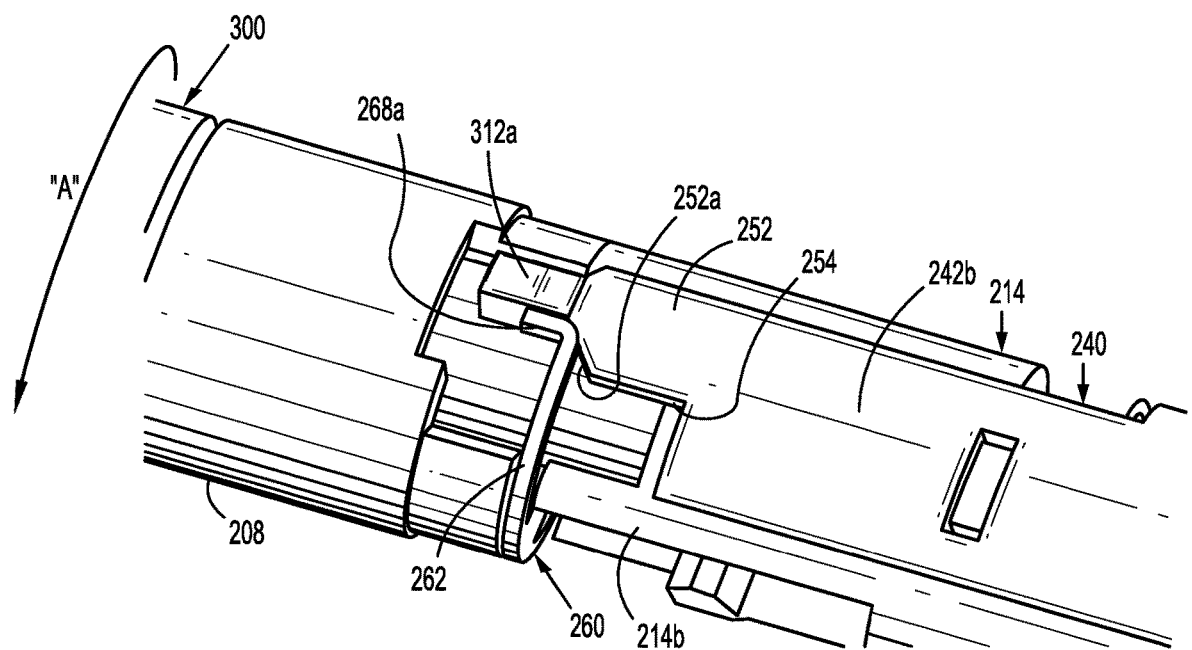
FIG. 3B is an enlarged operational view of the distal portion of the adapter assembly shown in FIG. 1B coupled with the loading unit shown in FIG. 1C.
Figure 4:
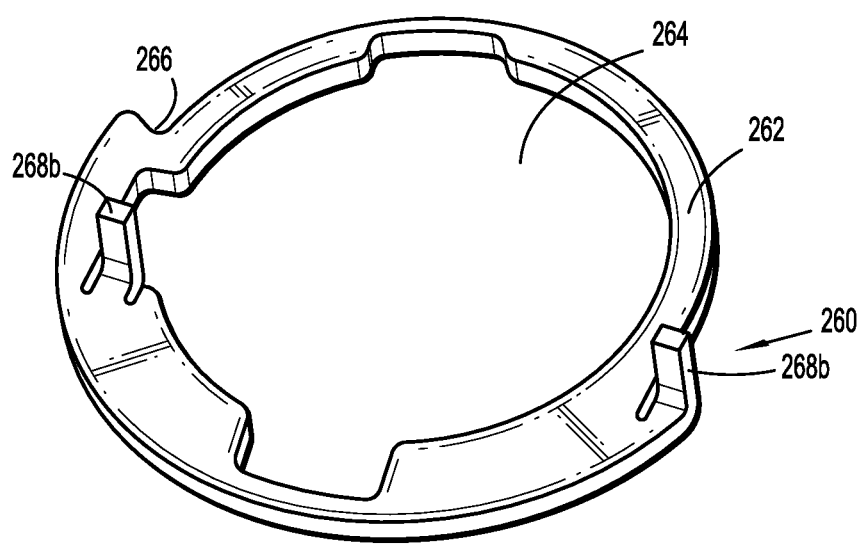
FIG. 4 is a perspective view of an annular member of the adapter assembly shown in FIG. 3A.

With reference to FIGS. 3A and 3B, distal end portion 242b of locking bar 240 includes an extension 252 having a tapered portion 252a. Distal end portion 242b of locking bar 240 further includes a cutout portion 254 configured to accommodate a first lug 312a of loading unit 300 (see FIG. 5A), as described in greater detail below. Locking bar 240 further includes a biasing member, e.g., a coil spring 255 that resiliently biases locking bar 240 toward the distal/locking position, in which ring member 244 of locking bar 240 actuates or depresses switch 220.

With reference to FIGS. 3A-5B, adapter assembly 200 includes annular member 260, which is rotatably disposed between a distal end 214b of inner housing 214 and distal cap 208 of elongated body 204. Annular member 260 includes a ring body 262 having a substantially planar configuration. Ring body 262 defines a cylindrical passageway 264 therethrough configured for disposal of loading unit 300. It is contemplated that a portion or portions of annular member 260 may be ring-shaped or that all of annular member 260 may be ring-shaped. Ring body 262 defines a groove or notch 266 in an outer surface thereof configured to capture a distal end 282b of leaf spring 280 (see FIGS. 6A and 6B) therein, as described in greater detail below.

Annular member 260 further includes a first appendage or tab 268a and a second appendage or tab 268b, each extending perpendicularly from ring body 262. Tabs 268a, 268b are circumferentially disposed on ring body 262 and radially spaced from one another along the outer surface of ring body 262. First tab 268a of annular member 260 abuts extension 252 of locking bar 240 to maintain locking bar 240 in the proximal/non-locking position, as shown in FIGS. 3A and 3B. First tab 268a of annular member 260 is configured to interface or engage with a first protrusion or first lug 312a (FIGS. 3B, 5A, and 5B) of loading unit 300 upon coupling loading unit 300 with adapter assembly 200, such that annular member 260 is rotatable by and with loading unit 300.

Annular member 260 is rotatable between a first orientation and a second orientation. In the first orientation, as shown in FIGS. 3A and 3B, first tab 268a of annular member 260 engages extension 252 of locking bar 240. First tab 268a prevents distal movement of locking bar 240 from the proximal/non-locking position to the distal/locking position, thereby maintaining ring member 244 of locking bar 240 out of engagement with switch 220. Accordingly, first tab 268a of annular member 260 maintains locking bar 240 in the proximal/non-locking position, out of engagement with switch 220, and also provides an interface between loading unit 300 and annular member 260.

Figure 5B:
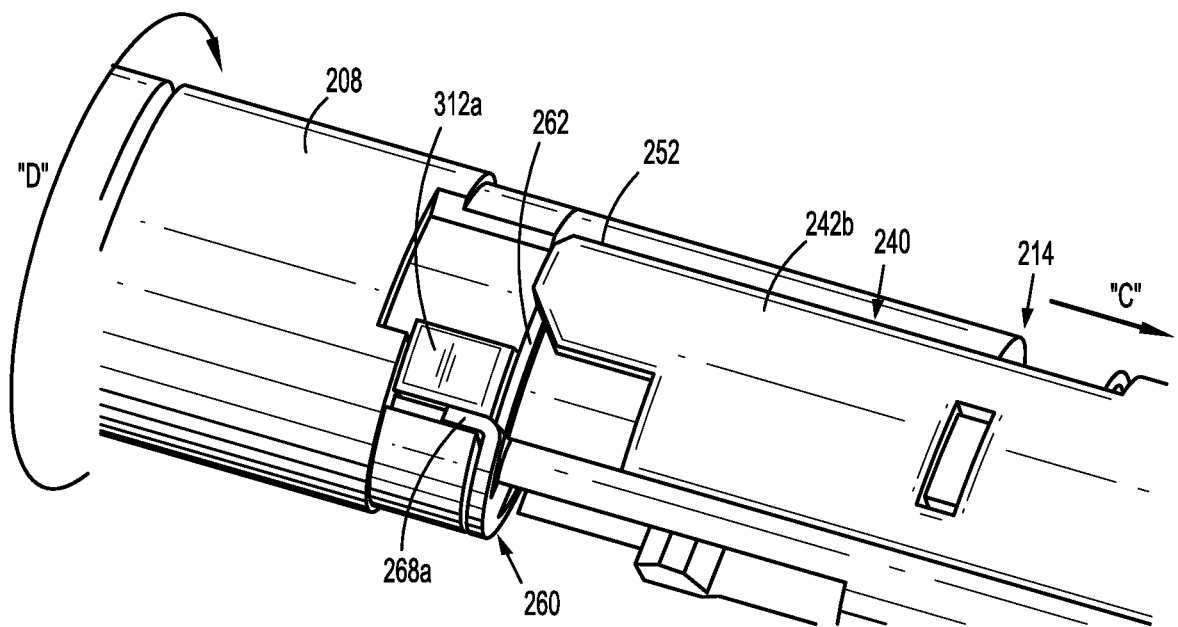
FIG. 5B is an enlarged operational view of the distal portion of the adapter assembly shown in FIG. 1B non-lockingly engaged with the loading unit shown in FIG. 1C.

In the second orientation, as shown in FIGS. 5A and 5B, first tab 268a of annular member 260 is disengaged from extension 252 of locking bar 240 thereby permitting locking bar 240 to move distally to toggle switch 220.

Figure 6A:
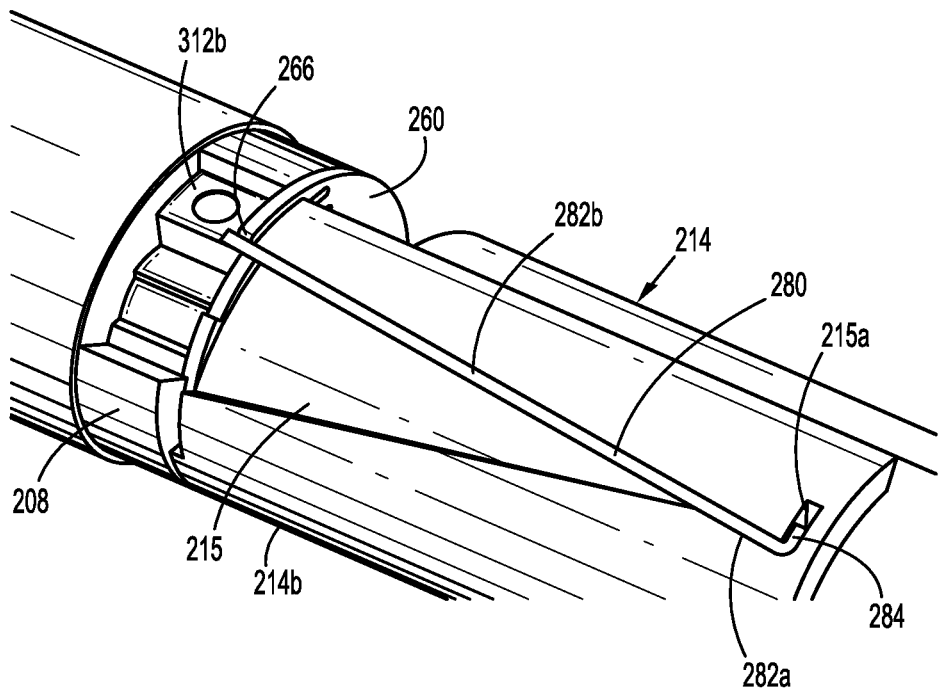
FIG. 6A is an enlarged operational view of the distal portion of the adapter assembly shown in FIG. 1B engaged with the loading unit of FIG. 1C, illustrating the annular member and a biasing member in a first orientation.
Figure 6B:
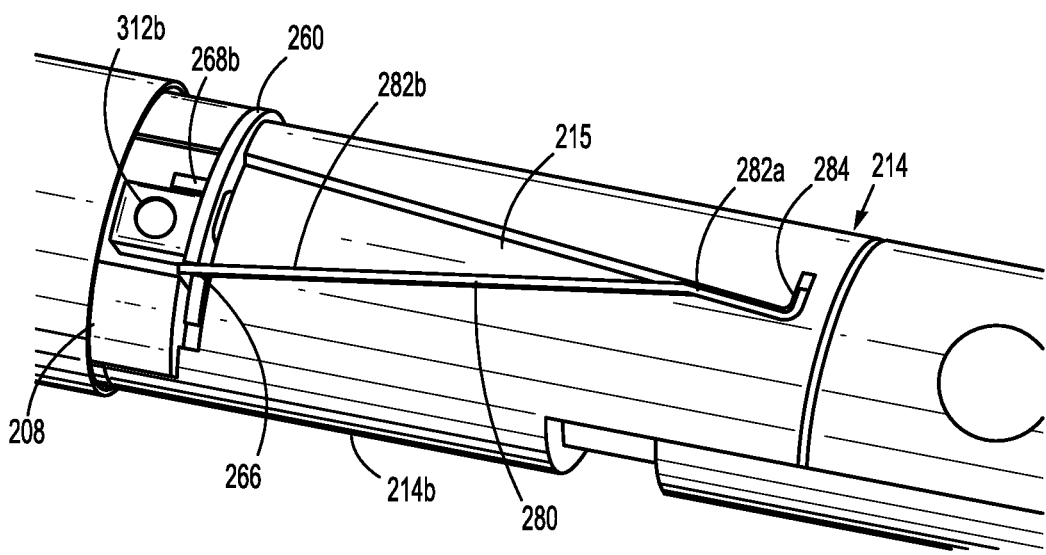
FIG. 6B is an enlarged operational view of the distal portion of the adapter assembly shown in FIG. 1B engaged with the loading unit of FIG. 1C, illustrating the annular member and the biasing member in a second orientation.

With reference to FIGS. 6A and 6B, an opposite radial side of adapter assembly 200 is shown. Adapter assembly 200 further includes a biasing member, e.g., leaf spring 280. Leaf spring 280 is disposed in a cavity 215 defined in distal end 214b of inner housing 214 of elongated body 204. Cavity 215 has a substantially triangular configuration. In embodiments, cavity 215 may be of any suitable shape for housing the lead spring 280, such as, for example, arcuate, oblong, squared, oval, tapered, uniform, non-uniform, and/or polygonal. Leaf spring 280 has a proximal end 282a and a distal end 282b. Proximal end 282a has a bent portion or tang 284 fixed in a correspondingly shaped channel 215a of cavity 215. Distal end 282b is disposed in notch 266 of annular member 260. Distal end 282b is pivotable about proximal end 282a to sweep across cavity 215 upon rotation of annular member 260 between the first and second orientations. The resilient bias of leaf spring 280 resists and/or prevents annular member 260 from rotating from the first orientation to the second orientation. In this way, leaf spring 280 maintains first tab 268a of annular member 260 in abutment with extension 252 of locking bar 240, thereby maintaining locking bar 240 in the proximal/non-locking position, out of engagement with switch 220, until loading unit 300 is engaged to adapter assembly 200.

In operation, with reference to FIGS. 3B, and 5A-6B, loading unit 300 is inserted within distal cap 208 of elongated body 204 to abut first lug 312a of loading unit 300 with first tab 268a of annular member 260, as shown in FIG. 3B. Loading unit 300 is then rotated, in a direction indicated by arrow "A" in FIG. 3B, to overcome the resilient bias of leaf spring 280 thereby rotating annular member 260 from the first orientation to the second orientation. Rotation of annular member 260 from the first orientation to the second orientation disengages first tab 268a of annular member 260 from extension 252 of locking bar 240 such that the distally-oriented bias of locking bar 240 moves locking bar 240, in the direction indicated by arrow "B" in FIG. 5A, toward the distal/locking position. In the distal/locking position, first lug 312a of loading unit 300 is captured in an enclosure 284 defined by extension 252 of locking bar 240, first tab 268a of annular member 260, and distal cap 208, thereby preventing loading unit 300 from decoupling from adapter assembly 200.

In the distal/locking position, ring member 244 of locking bar 240 is in engagement with switch 220 to toggle switch 220, as shown in FIG. 2B. When switch 220 is toggled, switch 220 communicates to handle assembly 100 an indicator that loading unit 300 is lockingly engaged to adapter assembly 200 and/or parameters pertaining to loading unit 300. The parameter may include a serial number of a loading unit, a type of a loading unit, a size of a loading unit, a staple size, information identifying whether the loading unit has been fired, a length of a loading unit, and/or a maximum number of uses of a loading unit.

To selectively release loading unit 300 from adapter assembly 200, locking bar 240 is translated in a proximal direction, indicated by arrow "C" in FIG. 5B, toward the proximal/non-locking position, via movement of button 203 (see FIG. 1A) on knob housing 202. Upon locking bar 240 entering the proximal/non-locking position, ring member 244 of locking bar 240 disengages switch 220, which communicates to handle assembly 100 that loading unit 300 is no longer lockingly engaged with adapter assembly 200 and not ready for operation.

In the proximal/non-locking position, extension 252 of locking bar 240 is no longer blocking first lug 312a of loading unit 300 and loading unit 300 can be rotated. Loading unit 300 is rotated, in a direction indicated by arrow "D" in FIG. 5B, to move first lug 312a of loading unit 300 out of enclosure 284. The rotation of loading unit 300 also drives the rotation of annular member 260 from the second orientation to the first orientation via the mating engagement of second lug 312b of loading unit 300 and second tab 268b of annular member 260 (see FIG. 6B). As annular member 260 rotates from the second orientation to the first orientation, leaf spring 280 pivots, due to its resilient bias, from a deflected state (see FIG. 6B) to its non-deflected state (see FIG. 6A), in which first tab 268a of annular member 260 is in engagement with extension 252 of locking bar 240 to maintain locking bar 240 in the proximal/non-locking position and out of engagement with switch 220.

To fully disengage loading unit 300 from adapter assembly 200, loading unit 300 is axially translated, in a distal direction, through distal cap 208, and out of elongated body 204 of adapter assembly 200. It is contemplated that upon handle assembly 100 detecting that loading unit 300 is not lockingly engaged to adapter assembly 200, power may be cut off from handle assembly 100, an alarm (e.g., audio and/or visual indication) may be issued, and combinations thereof.

While an electrical interface between loading unit 300, adapter assembly 200, and handle assembly 100 is shown and described, it is contemplated that any other form or communication is within the scope of the present disclosure, for transmitting any or all of the operating parameters and/or the life-cycle information from loading unit 300 to handle assembly 200, such as, for example, wireless communication, including various radio frequency protocols such as near field communication, radio frequency identification "RFID," BLUETOOTH® (owned by Bluetooth SIG, Inc.), etc.

Figure 7A:
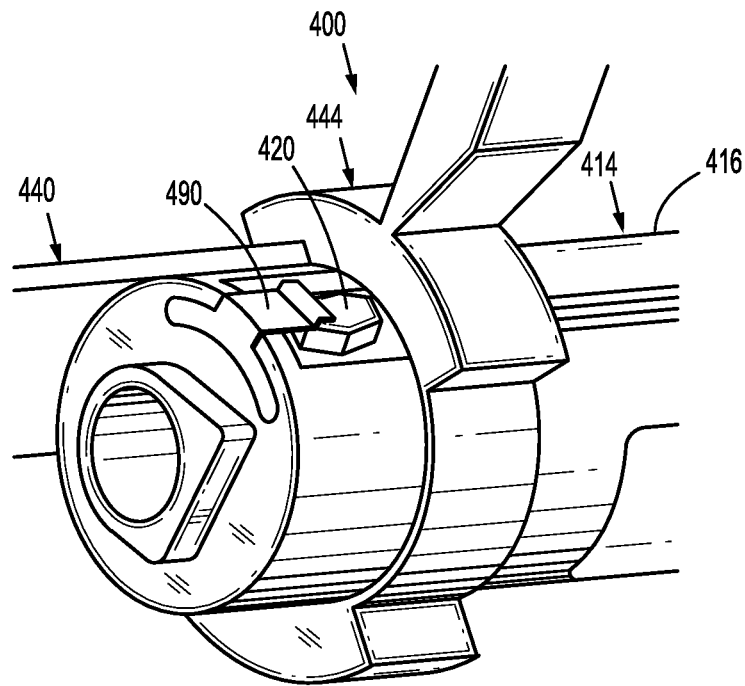
FIGS. 7A and 7B are alternate enlarged operational views of a proximal portion of an alternative embodiment of an adapter assembly in accordance with the principles of the present disclosure.
Figure 7B:
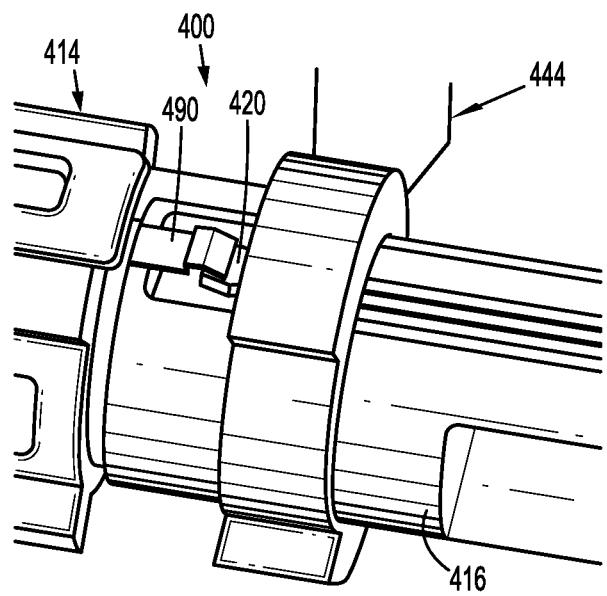

With reference to FIGS. 7A and 7B, an alternative embodiment of an adapter assembly 400, which is substantially similar to adapter assembly 200, is provided. Adapter assembly 400 includes an inner housing 414, similar to inner housing 214, an elongated member or locking bar 440, similar to locking bar 240, a switch 420, similar to switch 220, and an actuator board 490.

Inner housing 414 has a proximal end 416 disposed adjacent to a knob housing (not shown), similar to knob housing 202, and a distal end (not shown). Switch 220 is disposed within proximal end 416 of inner housing 414. Locking bar 440 includes a switch actuator or ring member 444, which is substantially similar to ring member 244 discussed above. Actuator board or tab 490 is attached to proximal end 416 of inner housing 414 and extends proximally therefrom to overlap switch 420. Actuator board 490 is configured to deflect into engagement with switch 420 upon a downwardly-oriented force being imparted thereon.

In operation, ring member 444 is translated from a proximal position, as shown in FIGS. 7A and 7B, to a distal position (not shown). In the proximal position, ring member 444 is out of engagement with actuator board 490, such that switch 420 is not actuated. In the distal position, ring member 444 overlaps actuator board 490 to deflect actuator board 490 into engagement with switch 420. As discussed above with reference to FIGS. 1A-6B and toggling of switch 220, upon a toggling of switch 420, handle assembly 100 detects that loading unit 300 is not lockingly engaged to adapter assembly 400.

Figure 8A:
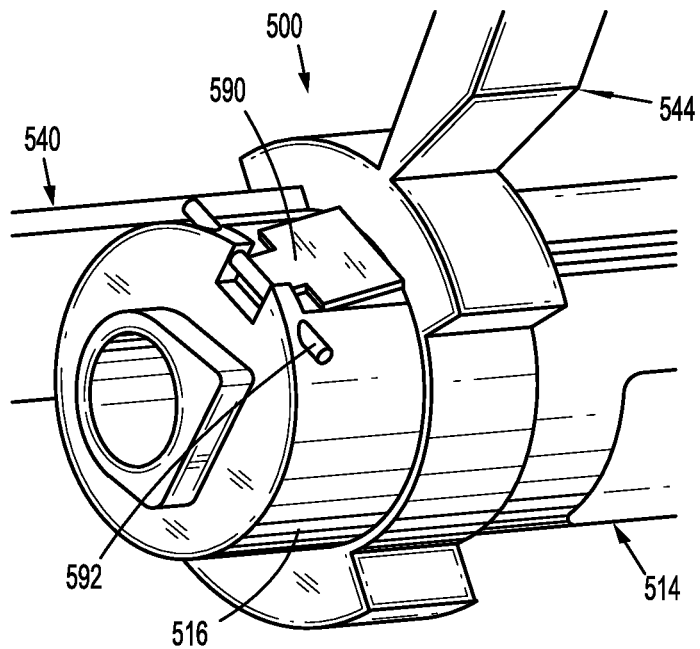
FIGS. 8A and 8B are alternate enlarged operational views of a proximal portion of another alternative embodiment of an adapter assembly in accordance with the principles of the present disclosure.
Figure 8B:
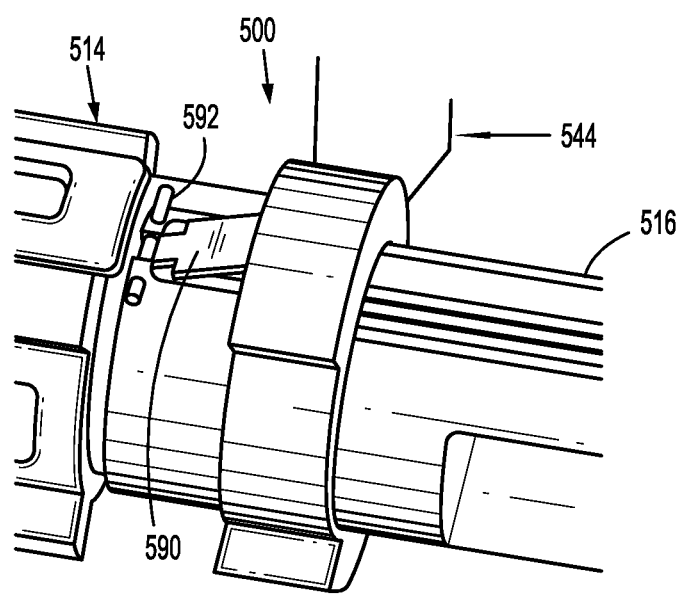

With reference to FIGS. 8A and 8B, another alternative embodiment of an adapter assembly 500, which is substantially similar to adapter assembly 200, is provided. Adapter assembly 500 includes an inner housing 514, similar to inner housing 214, an elongated member or locking bar 540, similar to locking bar 240, a switch (not shown), similar to switch 220, and an actuator board 590.

Inner housing 514 has a proximal end 516 disposed adjacent to a knob housing (not shown), similar to knob housing 202, and a distal end (not shown). The switch is disposed within proximal end 516 of inner housing 514. Locking bar 540 includes a switch actuator or ring member 544, similar to ring member 244 discussed above. Actuator board or tab 590 is attached to proximal end 516 of inner housing 514 and extends proximally therefrom to overlap the switch. Actuator board 590 is pivotably connected to proximal end 516 of inner housing 514 via a pivot pin or rod 592.

In operation, ring member 544 is translated from a proximal position, as shown in FIGS. 8A and 8B, to a distal position (not shown). In the proximal position, ring member 544 is out of engagement with actuator board 590, such that the switch is not actuated. In the distal position, ring member 544 overlaps actuator board 590 to rotate actuator board 590 into engagement with the switch. As discussed above with reference to FIGS. 1A-6B, upon a toggling of the switch, handle assembly 100 detects that loading unit 300 is not lockingly engaged to adapter assembly 500.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

The invention claimed is:

1. A method of assembling a surgical instrument, the method comprising:
    coupling a surgical loading unit of the surgical instrument to a distal end portion of an adapter assembly of the surgical instrument;
    rotating an annular member of the adapter assembly out of a path of an elongated member of the adapter assembly;
    moving the elongated member of the adapter assembly in a distal direction to toggle a switch of the adapter assembly, wherein toggling the switch represents that the surgical loading unit is lockingly engaged with the adapter assembly; and
    abutting at least one appendage of the annular member against at least one protrusion of the surgical loading unit upon coupling the surgical loading unit to the adapter assembly, wherein rotating the annular member includes rotating the annular member relative to the elongated member from a first orientation, in which the at least one appendage is engaged to a distal end portion of the elongated member to maintain the elongated member in a proximal position, to a second orientation, in which the at least one appendage is disengaged from the distal end portion of the elongated member such that the elongated member moves to a distal position to toggle the switch.

2. The method according to claim 1, further comprising decoupling the surgical loading unit from the adapter assembly, whereby the annular member rotates to the first orientation.

3. The method according to claim 1, further comprising rotating the surgical loading unit relative to the adapter assembly, wherein rotating the surgical loading unit causes the annular member to rotate.

4. The method according to claim 1, wherein the elongated member is resiliently biased toward the distal direction, such that the elongated member automatically moves in the distal direction to toggle the switch upon rotating the annular member out of the path of the elongated member.

5. The method according to claim 1, further comprising communicating, when the switch is toggled, to a handle assembly of the surgical instrument at least one of an indicator that the surgical loading unit is lockingly engaged with the adapter assembly or at least one parameter pertaining to the surgical loading unit.

6. The method according to claim 1, wherein when the elongated member is in the distal position, the at least one protrusion is captured between the at least one appendage and the distal end portion of the elongated member such that the surgical loading unit is lockingly engaged with the adapter assembly.

7. A method of assembling a surgical instrument, the method comprising:
    inserting a surgical loading unit of the surgical instrument into a distal end portion of an adapter assembly of the surgical instrument;
    rotating the surgical loading unit relative to the adapter assembly, thereby rotating an annular member of the adapter assembly, against a resilient bias of a biasing member that is engaged to the annular member, out of a path of a locking bar of the adapter assembly; and
    toggling a switch of the adapter assembly upon rotating the annular member out of the path of the locking bar.

8. The method according to claim 7, further comprising moving the locking bar in a distal direction, wherein moving the locking bar in the distal direction toggles the switch.

9. The method according to claim 8, wherein the locking bar is resiliently biased toward the distal direction, such that the locking bar automatically moves in the distal direction to toggle the switch upon rotating the annular member out of the path of the locking bar.

10. The method according to claim 7, wherein rotating the annular member includes rotating the annular member relative to the locking bar from a first orientation, in which the annular member prevents distal movement of the locking bar, to a second orientation, in which the locking bar moves distally to toggle the switch.

11. The method according to claim 10, further comprising decoupling the surgical loading unit from the adapter assembly, whereby the annular member rotates to the first orientation.

12. The method according to claim 11, wherein decoupling the surgical loading unit from the adapter assembly includes:
    rotating the surgical loading unit relative to the adapter assembly during which the biasing member transitions from a biased state to an unbiased state; and
    sliding the surgical loading unit distally out of from within the distal end portion of the adapter assembly.

13. The method according to claim 7, further comprising communicating, when the switch is toggled, to a handle assembly of the surgical instrument at least one of an indicator that the surgical loading unit is coupled to the adapter assembly or at least one parameter pertaining to the surgical loading unit.

14. The method according to claim 7, further comprising abutting at least one appendage of the annular member against at least one protrusion of the surgical loading unit upon inserting the surgical loading unit into the distal end portion of the adapter assembly.

15. The method according to claim 14, wherein rotating the annular member includes rotating the annular member relative to the locking bar from a first orientation, in which the at least one appendage is engaged to a distal end portion of the locking bar to maintain the locking bar in a proximal position, to a second orientation, in which the at least one appendage is disengaged from the distal end portion of the locking bar such that the locking bar moves to a distal position to toggle the switch.

16. The method according to claim 15, wherein when the locking bar is in the distal position, the at least one protrusion is captured between the at least one appendage and the distal end portion of the locking bar such that the surgical loading unit is lockingly engaged with the adapter assembly.

17. The method according to claim 7, wherein inserting the surgical loading unit into the distal end portion of the adapter assembly includes axially translating the surgical loading unit into the distal end portion of the adapter assembly.

18. The method according to claim 7, wherein the biasing member is a leaf spring that pivots, due to the rotation of the annular member, from a non-deflected state to a deflected state, wherein in the non-deflected state the leaf spring maintains the annular member in engagement with the locking bar to maintain the locking bar in a proximal position and out of engagement with the switch.

* * * * *